US00PP08736P

United States Patent [19]

van Zanten

[11] Patent Number: Plant 8,736

[45] Date of Patent: May 17, 1994

[54] ALSTROEMERIA NAMED NEVADA

[75] Inventor: G. E. Veldhuyzen van Zanten, Hillegom, Netherlands

[73] Assignee: Koninklijke van Zanten, Hillegom, Netherlands

[21] Appl. No.: 964,361

[22] Filed: Oct. 21, 1992

[51] Int. Cl.[5] ..... A01H 5/00

[52] U.S. Cl. ..... Plt./87.1

[58] Field of Search ..... Plt. 87.1

*Primary Examiner*—James R. Feyrer

*Assistant Examiner*—Erich Veitenheimer

*Attorney, Agent, or Firm*—Tilton, Fallon, Lungus & Chestnut

[57] ABSTRACT

A new and distinctive alstroemeria cultivar particularly distinguished by its medium-size flowers having generally an ivory-white flower color, leaves and internodes being shorter than common varieties, pedicels having a horizontal setting on the main stem and high productivity.

1 Drawing Sheet

Background of the New Plant

This alstroemeria cultivar originated as a hybrid seedling produced in my nursery at Hillegom, The Netherlands by my crossing of two plants, hereinafter identified, selected from a field of various alstroemeria varieties maintained at my nursery gor breeding purposes. This particular seedling was selected from those produced by the said hybrid because of the very unusual flower coloration on a plant having abundant foliage and very favorable growth characteristics. This selected seedling was propagated by me at Hillegom by dividing its roots with very satisfactory results and thereafter this selected plan was propagated through several successive generations in the same manner which demonstrated conclusively that the novel characteristics of the originally selected seedling would be maintained from gneration to generation and its homogeneity would be firmly established.

Nevada is similar to Alstroemeria named Stalibla (U.S. Plant Pat. No. 7,886) and Alstroemeria named Stablaco (U.S. Plant Pat. No. 4,930). Below in a tabular format, is a side-by-side comparison of the varieties.

| | Stalibla (U.S. Plant Pat. No. 7,886) | Stablaco (U.S. Plant Pat. No. 4,930) | Nevada (Ser. No. 07/964,361) |
|---|---|---|---|
| Outer Petal Color | 158-C (body) 158-C (base) | 158-C-D (body) 48-D (base) | 155 B/C/2d |
| Inside Petal Color | 2/3 of the inside portion has a color of 13-B with the upper most portion 158-C | 158-C-D (body) 48-D (base) | 155 B/2d |
| Reverse Side Color | 158-C (Outer Petal) 158-C (Inside Petal outer portion) 12-C (Inside Petal inner portion) | 48-D | 155-B |
| Color of Stripes | Brown | Brown | Yellow |
| Leaf Shape | Elliptic | Elliptic | Lanceolate |
| Fruit | Unknown | Not Fertile | Fertile |
| Peduncle | about 2 cm. | about 4 cm. | 10–15 cm. |

Description of the Drawing

My new alstroemeria plant is illustrated by the accompanying photographic drawing which, in full color, shows the form and coloration of the flowers as they appear with relatively close spacing in a raceme manner at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new alstroemeria plant as observed from plants grown under greenhouse conditions in Hillegom, Holland, withthe stated flower colors being according to The R.H.S. Colour Chart of The Royal Horticultural Society of London, England.

THE PLANT

Origin: Seedling.

Parentage:

*Seed parent.*—Unreleased, unnamed, unnumbered proprietary hybrid.

*Pollen parent.*—Unreleased, unnamed, unnumbered proprietary hybrid.

These parent plants are so identified in my business records of the present cultivar maintained at the office of the Hillegom nursery and the production of the aforementioned hybird and the selected seedling are also there recorded.

Classification:

*Botanic.*—Alstroemeria hybrid.

*Commercial.*—Alstroemeria.

Form: A tall, upright bush having a strong and vigorous spreading growth habit. In the first season, the ground covered by a single plant is about 20×20 cm. In the second season, the ground covered by the plant is about 30×30 cm. The plant is lifted after 2 years.

Height: About 120–160 cm.

Character: Unbranched stem till umbel, stem arise from rhizomes.

Main stem length: About 120–150 cm. depending upon the season.

Foliage:

*Quantity.*—Abundant.

*Number of leaves.*—30–40/stem.

*Size and shape of leaf.*—The leaf is of a generally lanceolate shape and about 15 cm in length. The width of the leaf is 2.5–3 cm.
*Margin type.*—Smooth/equal.
*Texture.*—Glossy.
*Color.*—Upper side — Light Green. Under side .— Light Green.

Rhizomes:
*Size.*—½ cm.
*Color.*—Plae White.

THE BUD

Size:
*Diameter.*—1–1.5 cm.
*Length.*—5–6 cm.
Shape: Ovoid.
Color of petals:
*When petals first divide.*—Green yellow.
When petals begin to unfurl—yellow ivory white.
Peduncle:
*Length.*—10–15 cm.
*Character.*—Erect.
*Color.*—Green.
*Rate of opening.*—Fast.
Calyo:
*Shape.*—Pear-shaped.
*Aspect.*—Smooth.

THE FLOWER

Blooming habit: Continuous and profusely from early Spring through mid-season and Fall.
Size of bloom: Medium.
*Diameter.*—About 5 cm.
*Depth.*—About 3 cm.
Borne: Cluster.
Shape: When bloom matures, cup like umbel.
Number of petals: 6.
Number of florets: 4–6 bud-forming florets per stem in an umbel arrangement.
Shape of outside perianth: Wide obovate.
Shape of inside perianth: Long abovate.
Texture: Soft.
Appearance: Satiny.
Color:
*Outer petals.*—Body RHS 155B, 155C, or 2D.
*Reverse side.*—RHS 155B Ivory White.
*Inside petals.*—RHS 155B or 2D.
*Reverse side.*—RHS 155B.
Discoloration after full bloom: No.
Persistence: Some persistence. No special persistence noted for Nevada.
Lasting quality:
*On the plant.*—About 14–18 days.
*As cut flower.*—About 12–16 days.
Dates for first and last bloom: In Holland, planting time is in November. The first bloom will appear in November.
Known disease resistances/susceptibilities: None.
Fertilizer or growing condition requirements: None.

THE REPRODUCTIVE ORGANS

Stamens:
*Number.*—Six.
Arrangement: Three stamens are arranged in two rings and in the middle of this arrangement grows the pistil.
Anthers:
*Size.*—About 0.5 cm.
*Color.*—RHS 162B.
Filaments:
*Length.*—About 4 cm.
*Color.*—Yellow.
Pollen:
*Color.*—Yellow Brown.
Pistils:
*Number.*—One.
Style:
*Length.*—About ⅔ cm.
*Color.*—White/Yellow.
Stigmas: White/Yellow.
Fertility: The fruit is fertile.
Shape: Ovoid.
Color at maturity: Green.
Seed description: The seed capsule consists of three compartments and has a total of 6 attachments. The capsule is light green and is without anthocyanin coloring.

I claim:

1. A new and distinctive hybrid alstroemeria plant, substantially as herein shown and described, characterized in particular by its medium size flowers, the outer petals of which are in general of an ivory white color and inner petals being of an ivory white color with many yellow longitudinally extending pencil stripes, said plant having between 30 to 40 leaves per stem.

* * * * *

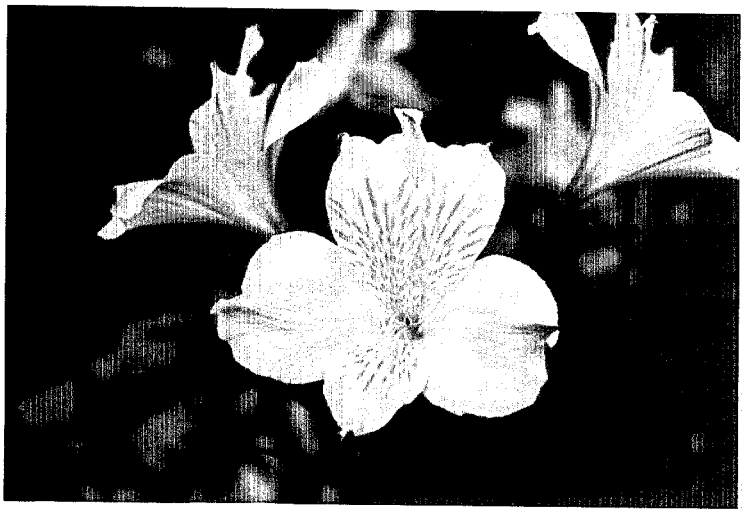

UNITED STATES PATENT AND TRADEMARK OFFICE

CERTIFICATE OF CORRECTION

PATENT NO. : PP08736

DATED : May 17, 1994

INVENTOR(S) : van Zanten

It is certified that error appears in the above-indentified patent and that said Letters Patent is hereby corrected as shown below:

Column 1, line 7, delete "gor" and insert -- for --.
Column 2, line 15, delete "withthe" and insert -- with the --.
Column 3, line 9, delete "1/2" and insert -- 3/4 --.
line 10, delete "Plae" and insert -- Pale --.
line 41, delete "abovate" and insert -- obovate --.

Signed and Sealed this

First Day of August, 1995

Bruce Lehman

*Attest:*

BRUCE LEHMAN

*Attesting Officer*

*Commissioner of Patents and Trademarks*